United States Patent [19]
Shiokawa et al.

[11] Patent Number: 5,463,095
[45] Date of Patent: Oct. 31, 1995

[54] PROCESS FOR THE PRODUCTION OF ESTERS

[75] Inventors: Yoshihiro Shiokawa; Tadayoshi Takefumi; Shunichi Matsumoto; Yoshifumi Sato, all of Kurashiki, Japan

[73] Assignee: Mitsubishi Gas Chemical Company, Inc., Tokyo, Japan

[21] Appl. No.: 260,237

[22] Filed: Jun. 14, 1994

[30] Foreign Application Priority Data

| Jun. 15, 1993 | [JP] | Japan | 5-143679 |
|---|---|---|---|
| Feb. 10, 1994 | [JP] | Japan | 6-016380 |
| Feb. 28, 1994 | [JP] | Japan | 6-030243 |
| Mar. 10, 1994 | [JP] | Japan | 6-040080 |
| Mar. 25, 1994 | [JP] | Japan | 6-055787 |

[51] Int. Cl.$^6$ ............................ C07C 51/15
[52] U.S. Cl. .......... 554/130; 554/150; 554/151; 560/206; 560/233
[58] Field of Search ............ 554/130, 151, 554/150; 560/206, 233

[56] References Cited

U.S. PATENT DOCUMENTS

| 3,005,846 | 10/1961 | Friedman et al. | 554/130 |
|---|---|---|---|
| 3,052,698 | 9/1962 | Friedman et al. | 260/410.9 |
| 4,590,293 | 5/1986 | Pascoe | 560/233 |
| 4,894,188 | 1/1990 | Takahashi et al. | 260/410.9 |

FOREIGN PATENT DOCUMENTS

| 0091604 | 10/1983 | European Pat. Off. |
|---|---|---|
| 1174209 | 12/1969 | United Kingdom . |
| 2101591 | 1/1983 | United Kingdom . |

*Primary Examiner*—José G. Dees
*Assistant Examiner*—Deborah D. Carr
*Attorney, Agent, or Firm*—Wenderoth, Lind & Ponack

[57] ABSTRACT

A process for the production of esters, comprising allowing an olefin, carbon monoxide and an alcohol to react in the presence of hydrogen fluoride, in which the esters can be produced at high yields at a low temperature for a short period of time, the esters can be easily separated from a reaction solution, hydrogen fluoride can be recycled, the esters can be produced at low cost, a mixture of esters can be easily produced, the kinetic viscosity of the mixture of the esters can be easily adjusted and the coloring of, and an increase in the viscosity of, the esters can be prevented.

11 Claims, 3 Drawing Sheets

PROCESS FOR THE PRODUCTION OF ESTERS

BACKGROUND OF THE INVENTION

1. Field of the Invention

The present invention relates to a process for the production of esters for use in a variety of products such as perfumes, jet engine oils, grease for use at a low temperature, heat-resistant engine oils, refrigerating machine oils, rubbers, inks and coating compositions. More specifically, it relates to a process for the production of a mixture of esters from an olefin, carbon monoxide and an alcohol, which mixture is advantageously used as an engine oil and a refrigerating machine oil.

2. Description of the Prior Art

Conventionally, an ester is produced by the reaction of dehydration in which a fatty acid and an alcohol are heated in the presence of a catalyst, as is described, e.g., in U.S. Pat. No. 5,202,044. The catalyst used for the above dehydration is selected from acid catalysts such as sulfuric acid and p-toluenesulfonic acid and organic titanate compounds such as tetrapropyl titanate.

The reaction of the above dehydration is an equilibrium reaction, and an excess of an alcohol is used. The reaction is promoted by removing formed water from the reaction system. Generally, however, the reaction rate is low, and it requires a long period of time to complete the reaction. Further, for producing an ester, for example, from a branched fatty acid such as rico-acid type, it is required to proceed with the reaction at a high temperature of at least 200° C. for at least 10 hours. As a result, it is required to use a large-volume reactor of a high-quality material, and it requires an additional cost.

For avoiding the reaction which is carried out at a high temperature for a long period of time, JP-A-4-314793 and JP-A-5-1291 propose a method in which an ester is produced through an acid chloride.

In the above method of the esterification through an acid chloride, however, it is first required to produce the acid chloride from a carboxylic acid, and for this purpose, acid chlorides of inorganic acids such as phosphorus trichloride, phosphorus pentachloride or thionyl chloride are used. These acid chlorides of inorganic acids are difficult to handle, and require complicated steps.

As described above, in the conventional processes for the production of esters, the reaction rate is low and it is required to use a large-volume reactor formed of a high-quality material when they are produced by the dehydration reaction between fatty acids and alcohols. Further, in the method in which an ester is formed through an acid chloride, a complicated step is required, since acid chloride of inorganic acid is used.

Further, esters are used in various fields as described above, and esters having performances required in various fields are selected or esters having different performances are mixed. For example, in various engine oils and refrigerating machine oils, the kinematic viscosity is particularly important, and the kinematic viscosity is adjusted by changing combinations of fatty acids and alcohols or by mixing a low-viscosity ester with a high-viscosity ester. For carrying out the esterification of various combinations, it is required to purchase or synthesize various raw materials, and it is also required to carry out the reaction under conditions suitable for the raw materials. For this reason, the reaction procedures are complicated, and it is difficult to produce various products efficiently. Further, when a low-viscosity ester and a high-viscosity ester are mixed, it is difficult in many cases to satisfy the performance and physical properties required.

SUMMARY OF THE INVENTION

It is an object of the present invention to provide a process for the production of esters at high yields at a low temperature for a short period of time.

It is another object of the present invention to provide a process for the production of esters, by which esters can be easily separated from a reaction solution, hydrogen fluoride can be recycled, and the esters can be produced at a low cost.

It is further another object of the present invention to provide a process for the production of esters, by which a mixture of esters can be easily produced and the kinetic viscosity of the mixture of esters can be easily adjusted.

It is still further another object of the present invention to provide a process for the production of esters, which permits the facile recovery of hydrogen fluoride from a reaction solution in an esterification step.

It is yet another object of the present invention to provide a process for the production of esters, which permits the efficient prevention of the coloring of, and an increase in the viscosity of, the esters which are separated from a reaction solution in an esterification step and purified.

According to the present invention, there is provided a process for the production of esters, which comprises allowing an olefin, carbon monoxide and an alcohol to react in the presence of hydrogen fluoride.

According to the present invention, there is also provided a process for the production of esters, which comprises the step of reacting an olefin with carbon monoxide in the presence of hydrogen fluoride to synthesize an acyl fluoride and the esterification step of reacting the acyl fluoride with an alcohol.

According to the present invention, there is further provided a process for the production of esters, which comprises the step of reacting an olefin with carbon monoxide in the presence of hydrogen fluoride to synthesize an acyl fluoride and the esterification step of reacting the acyl fluoride with an alcohol, wherein an olefin having at least 4 carbon atoms is used as the olefin and the reaction temperature and/or the reaction pressure in the step of synthesizing the acyl fluoride are/is properly changed to obtain a mixture of esters having an adjusted kinetic viscosity.

According to the present invention, there is still further provided a process for the production of esters, which comprises the step of reacting an olefin with carbon monoxide in the presence of hydrogen fluoride to synthesize an acyl fluoride and the esterification step of reacting the acyl fluoride with an alcohol, wherein a solution containing the acyl fluoride is distilled under the reflux of a saturated hydrocarbon having a higher boiling point than the acyl fluoride and being inert to the acyl fluoride to reduce the formation of byproducts in the esterification step.

According to the present invention, further, there is provided a process for the production of esters, which comprises the step of reacting an olefin with carbon monoxide in the presence of hydrogen fluoride to synthesize an acyl fluoride and the esterification step of reacting the acyl fluoride with an alcohol, wherein a reaction solution containing esters obtained in the esterification step are distilled under the reflux of a saturated hydrocarbon having a higher boiling point than the acyl fluoride and being inert to the acyl fluoride to separate and recover hydrogen fluoride for recycling.

Further, according to the present invention, there is provided a process for the production of esters, which comprises the step of reacting an olefin with carbon monoxide in the presence of hydrogen fluoride to synthesize an acyl fluoride and the esterification step of reacting the acyl fluoride with an alcohol, wherein there is further carried out a purification step in which a esters-containing reaction solution remaining after the separation of the hydrogen fluoride is washed with water and distilled and the purified esters are catalytically hydrogenation-treated to obtain decolored esters having a low acid value.

DETAILED DESCRIPTION OF THE INVENTION

The olefin used as a raw material in the present invention includes propylene, butylene, isobutylene, pentene, hexene and octene.

The alcohol used in the present invention includes monohydric alcohols such as methanol, ethanol, propanol, isopropanol, butanol, pentanol, hexanol, heptanol and octanol; and polyhydric alcohols such as neopentyl glycol, trimethylol ethane, trtmethylol propane, pentaerythritol, ethylene glycol, propylene glycol, glycerol and sorbitol.

The amount of the hydrogen fluoride used in the present invention per mole of the olefin is at least 5 mol, preferably 5 to 30 mol, particularly preferably 7 to 15 mol. When the molar ratio of the hydrogen fluoride to the olefin is lower than 5, the degree of occurrence of side reactions increases, and the yields of the acyl fluoride and esters are low. When the above molar ratio is greater than 30, there is no further improvement in the yields, and economically disadvantageously, a reactor having a large volume is required. In the present invention, the hydrogen fluoride may be used in combination with boron trifluoride as a catalyst.

The equivalent ratio of OH group of the alcohol to the olefin is 2 or less, preferably 0.7 to 1.5. When the amount of the alcohol is too large, the amount of unreacted alcohol to be recovered is large. When the amount of the alcohol is too small, the yield of the esters is low.

The process of the present invention includes a method (1) in which the olefin and carbon monoxide are allowed to react in hydrogen fluoride and then the alcohol is allowed to react with the reaction product, a method (2) in which the olefin is fed to a reactor containing hydrogen fluoride, carbon monoxide and the alcohol to allow the olefin, the carbon monoxide and the alcohol to react, and a method (3) in which the olefin and the alcohol are simultaneously fed into a reactor containing hydrogen fluoride and carbon monoxide to allow the olefin, the carbon monoxide and the alcohol to react, although the process of the present invention is not limited to these methods.

In the method (1) in which the olefin and carbon monoxide are allowed to react in hydrogen fluoride and then the reaction product is allowed to react with the alcohol, it is assumed that an acyl fluoride is formed by the reaction between the olefin and carbon monoxide in hydrogen fluoride and that esters and hydrogen fluoride are formed by the reaction between the acyl fluoride and the alcohol. In this method (1), advantageously, esters can be produced at high yields.

In the method (1), the pressure for the reaction between the olefin and carbon monoxide in hydrogen fluoride is 100 kg/cm$^2$G, preferably 10 to 80 kg/cm$^2$G. When this reaction pressure is low, the yield of the acyl fluoride is low. However, even when the reaction pressure is made higher than 100 kg/cm$^2$G, there is almost no improvement in the yield, and industrially disadvantageously, the cost of an apparatus therefor increases.

The amount of the carbon monoxide used for the reaction between the olefin and the carbon monoxide is determined depending upon the reaction pressure. The above-specified reaction pressure is a reaction pressure when high-purity carbon monoxide is used. When the gas of the carbon monoxide contains a considerable amount of inert gas, the partial pressure of carbon monoxide is to be taken as the reaction pressure.

Although differing depending upon the olefin, the temperature required for the reaction between the olefin and carbon monoxide is generally −30° to 70° C., preferably −20° to 50° C. When the reaction temperature is too high, the amount of byproducts increases and the yield of the acyl fluoride decreases. When the reaction temperature is too low, economically disadvantageously, the reaction rate is low.

The reaction of the product (acyl fluoride) from the olefin and carbon monoxide with the alcohol may be carried out under elevated pressure or atmospheric pressure. That is, the olefin and carbon monoxide are allowed to react under elevated pressure, and the reaction product may be allowed to react with the alcohol under the so-elevated pressure. Otherwise, the reaction product may be allowed to react with the alcohol after the pressure is reduced. The temperature for the reaction between the above reaction product and the alcohol is −10° to 70° C., preferably 0° to 50° C.

When the olefin and carbon monoxide are allowed to react in the presence of hydrogen fluoride, some olefins undergo isomerization, and the ester obtained by the esterification is an isomer mixture. The isomer mixture differs in composition depending upon the reaction temperature and pressure employed for the synthesis of the acyl fluoride, and proper reaction conditions are selected.

When an engine oil or a refrigerating machine oil is produced according to the process of the present invention, the process for the production of esters is divided, as explained above, into the step of synthesizing an acyl fluoride in which the olefin and carbon monoxide are allowed to react in the presence of hydrogen fluoride and the esterification step in which the acyl fluoride synthesis solution is allowed to react with the alcohol, the olefin used as a raw material in the step of synthesizing acyl fluoride is selected from olefins having at least 4 carbon atoms, and the reaction temperature or pressure is changed, whereby there can be obtained esters having an adjusted kinetic viscosity. In general, with an increase in the reaction temperature in the step of synthesizing acyl fluoride, the kinetic viscosity of a mixture of esters obtained in the esterification step increases. Further, with an increase in the reaction pressure in the step of synthesizing acyl fluoride, the viscosity of a mixture of esters obtained in the esterification step decreases.

In the method (2) in which the olefin is fed to a reactor containing hydrogen fluoride, carbon monoxide and the alcohol to allow the olefin, the carbon monoxide and the alcohol to react, and in the method (3) in which the olefin and the alcohol are simultaneously fed into a reactor containing hydrogen fluoride and carbon monoxide to allow the olefin, the carbon monoxide and the alcohol to react, the reaction pressure and temperature are generally the same as those employed for allowing the olefin and carbon monoxide in hydrogen fluoride, and these reaction pressure and temperature are properly selected depending upon the olefin and the alcohol used.

The reaction solution obtained in the process of the present invention is a solution of esters in hydrogen fluoride, and the process of the present invention hence does not particularly require any solvent. However, there may be used a solvent which does not affect the reaction. For example, there may be used a saturated hydrocarbon such as hexane, heptane or octane. The solvent may be used, for example, by a method in which the olefin is dissolved in the solvent and the solution is fed to a reactor.

In the above method in which the olefin, carbon monoxide and the alcohol are allowed to react in the presence of hydrogen fluoride, esters can be obtained at high yields by the reaction at a low temperature for a short period of time. However, some olefins and some alcohols form various byproducts due to the polymerization of the olefins or reactions of the olefins, carbon monoxide and alcohols. As a result, in some cases, the yield in the esterification is limited, and many distillation columns are required for separating the intended esters. In the method (1), therefore, the process for the production of esters is divided into the step of synthesizing an acyl fluoride in which the olefin and carbon monoxide are allowed to react in the presence of hydrogen fluoride and the esterification step in which the synthesized acyl fluoride is allowed to react with the alcohol, and the reaction solution from the step of synthesizing the acyl fluoride is distilled under the reflux of a saturated hydrocarbon, whereby the formation of byproducts in the esterification step decreases. As a result, the time required for operating the esterification step is decreased, and the yield in the esterification improves. Further, the separation and purification of the esters are facilitated.

According to the present invention, therefore, there is provided a process for the production of esters by allowing an olefin, carbon monoxide and an alcohol to react in the presence of hydrogen fluoride, which comprises the acyl fluoride synthesis step (i) in which the olefin and carbon monoxide are allowed to react in the presence of hydrogen fluoride, the acyl fluoride distillation step (ii) in which a reaction solution obtained in the step (i) is distilled together with an inert saturated hydrocarbon having a higher boiling point than the acyl fluoride, and the esterification step (iii) in which a mixture of hydrogen fluoride with the acyl fluoride, separated in the step (ii), is allowed to react with an alcohol.

In the acyl fluoride distillation step, a saturated hydrocarbon is used as a solvent for distilling the reaction solution from the acyl fluoride synthesis step. The saturated hydrocarbon has a higher boiling point than the acyl fluoride and is inert to the acyl fluoride. The above saturated hydrocarbon is selected from hexane, heptane, octane, nonane and decane. In this distillation step, the reaction solution from the acyl fluoride synthesis step is distilled under the reflux of the saturated hydrocarbon in a distillation column, and the saturated hydrocarbon is fed through an inlet provided at a lower position than that for the reaction solution containing the acyl fluoride. Hydrogen fluoride and high-purity acyl fluoride are separated the distillation column top and introduced to the esterification step. A mixture of saturated hydrocarbon with byproducts such as polymers of olefin formed in the acyl fluoride synthesis step is separated through the distillation column bottom. The saturated hydrocarbon is easily separated from the column bottom solution by distillation, and recycled.

The saturated hydrocarbon used in the acyl fluoride distillation step per mole of the olefin used in the acyl fluoride synthesis step is 0.5 to 2.0 mol, preferably 1.0 to 1.5 mol. When the molar ratio of the saturated hydrocarbon to the olefin is less than 0.5, it is difficult to obtain a high-purity acyl fluoride from the top of the distillation column. When the above molar ratio is greater than 2.0, uneconomically, the amount of heating energy is large, and the amount of the saturated hydrocarbon to be recovered is large.

The temperature for the distillation of the acyl fluoride differs depending upon the olefin and the saturated hydrocarbon used, while the temperature in the bottom of the distillation column is generally 100° to 250° C., preferably 120° to 200° C. The distillation is advantageously carried out under atmospheric pressure or elevated pressure, while the pressure for the distillation is preferably 0.5 to 1.0 kg/cm$^2$G.

The hydrogen fluoride is easily separated by distilling the esterification reaction solution obtained by the reaction of the acyl fluoride and alcohol in the method (1), the esterification reaction solution obtained by feeding the olefin in the presence of hydrogen fluoride, carbon monoxide and alcohol and reacting these in the method (2) and the esterification reaction solution obtained by simultaneously feeding the olefin and alcohol in the presence of hydrogen fluoride and carbon monoxide and reacting these in the method (3). The above-separated hydrogen fluoride can be recycled. Some esters can be recovered by pouring any one of the above esterification reaction solution into ice water and distilling a separated oil layer.

The esterification reaction solution is distilled with the distillation column (to be referred to as "HF-recovery distillation column" hereinafter) under the reflux of the saturated hydrocarbon, whereby the hydrogen fluoride is easily separated, and it can be recycled. When unreacted acyl fluoride is present, a saturated hydrocarbon which has a higher boiling point than the acyl fluoride and is inert to the acyl fluoride is used for recovering both this acyl fluoride and hydrogen fluoride from the column top. The above saturated hydrocarbon is selected from hexane, octane, nonane and decane. The reaction solution and saturated hydrocarbon are recovered from the bottom of the HF-recovery distillation column.

The amount of the saturated hydrocarbon used in the HF-recovery distillation column per mole of the olefin is 0.5 to 2.0 mol, preferably 1.0 to 1.5 mol. When the molar ratio of the saturated hydrocarbon to the olefin is less than 0.5, it is difficult to a sufficient amount of HF from the column top. When the above molar ratio is greater than 2.0, uneconomically, the amount of heating energy is large and the amount of saturated hydrocarbon to be recovered is large.

The temperature for the distillation in the HF-recovery distillation column differs depending upon the olefin and saturated hydrocarbon used, while the temperature in the bottom of the HF-recovery distillation column is generally 100° to 250° C., preferably 120° to 200° C. The distillation is processwise advantageously carried out under atmospheric pressure or elevated pressure, while the pressure for the distillation is preferably 0.5 to 1.0 kg/cm$^2$G.

In the above HF-recovery distillation column, the esterification reaction solution is distilled under the reflux of the saturated hydrocarbon, and it is preferred to feed the saturated hydrocarbon through a portion lower than a portion through which the esterification reaction solution is fed. The hydrogen fluoride is separated through the column top, and recycled to the acyl fluoride synthesis step. The esters, byproducts and the saturated hydrocarbon are separated through the column bottom. The saturated hydrocarbon is easily separated from the column bottom solution by distillation, and recycled to the HF-recovery distillation column.

In the present invention, the olefin, carbon monoxide and alcohol are allowed to react in the presence of hydrogen fluoride, the hydrogen fluoride is first recovered from the resultant reaction solution by the distillation under the reflux of the saturated hydrocarbon, and then the reaction solution is washed with water, purified by distillation and catalytic hydrogenation treatment, whereby the resultant ester(s) has an acid value of 0.02 mgKOH/g or less and is decolored. Therefore, ester(s) for use as an engine oil and a refrigerating machine oil can be very advantageously produced.

That is, after the hydrogen fluoride is recovered from the reaction solution, the reaction solution is purified by distillation and catalytically hydrogenation-treated. In the purification step, the column bottom solution from the HF-recovery distillation column is washed with water and subjected to distillation. The saturated hydrocarbon used in the HF-recovery distillation column is easily separated and recovered by simple distillation, and the recovered saturated hydrocarbon is recycled. Then, the reaction solution is purified and distilled to remove by-products, whereby the ester(s) is obtained. In the distillation for recovering the hydrogen fluoride, the ester(s) is colored. Further, due to the heating during the distillation of the ester, organic acids are formed, and the ester(s) has an increased acid value. The ester(s) which is colored and has an increased acid value is not suitable for use as a refrigerating machine oil and an engine oil. This problem can be overcome by catalytically hydrogenation-treating the reaction solution.

The distillation temperature for the recovery of the saturated hydrocarbon differs depending upon the saturated hydrocarbon used, The distillation temperature in the column bottom is generally 50° to 150° C., preferably 60° to 120° C. The distillation for the recovery of the saturated hydrocarbon is processwise advantageously carried out under reduced pressure, and the pressure for the distillation is preferably 10 to 60 torr.

The distillation temperature for obtaining the ester(s) differs depending upon the ester(s) synthesized. The distillation temperature in the column bottom is generally 100° to 300° C., preferably 150° to 280° C. The distillation for obtaining the ester(s) is processwise advantageously carried out under reduced pressure, and the pressure for the distillation is preferably 3 to 20 torr.

The catalytic hydrogenation treatment is carried out in the presence of a hydrogenating catalyst such as an Ru-, Pd- or Ni-containing catalysts. The amount of the catalyst per part of the ester(s) to be treated is 0.01 to 0.30 part by weight, preferably 0.04 to 0.20 part by weight. When the catalyst amount is smaller than the above lower limit, the hydrogenation treatment is not sufficient. When the catalyst amount is larger than the above upper limit, no further improvement is exhibited in the hydrogenation treatment, and industrially disadvantageously a reactor having a large volume is required.

Although differing depending upon the catalyst used, the temperature for the catalytic hydrogenation treatment is generally 70° to 110° C., preferably 80° to 100° C. When the above temperature is too low, the declaration of the ester(s) is insufficient, and the acid value does not decrease. When the temperature is too high, the ester(s) is colorless and transparent, but the acid value increases.

Although differing depending upon the catalyst used, the pressure for the catalytic hydrogenation treatment is generally 5 to 15 kg/cm$^2$G, preferably 7 to 10 kg/cm$^2$. When the above pressure is too low, the treatment rate is low and the decoloration is not sufficient. Further, even when the pressure is made higher than 15 kg/cm$^2$G, there is no improvement in acid value, and industrially disadvantageously, an additional cost is required for an apparatus.

The present invention will be explained hereinafter with reference to drawings.

Figure 1:
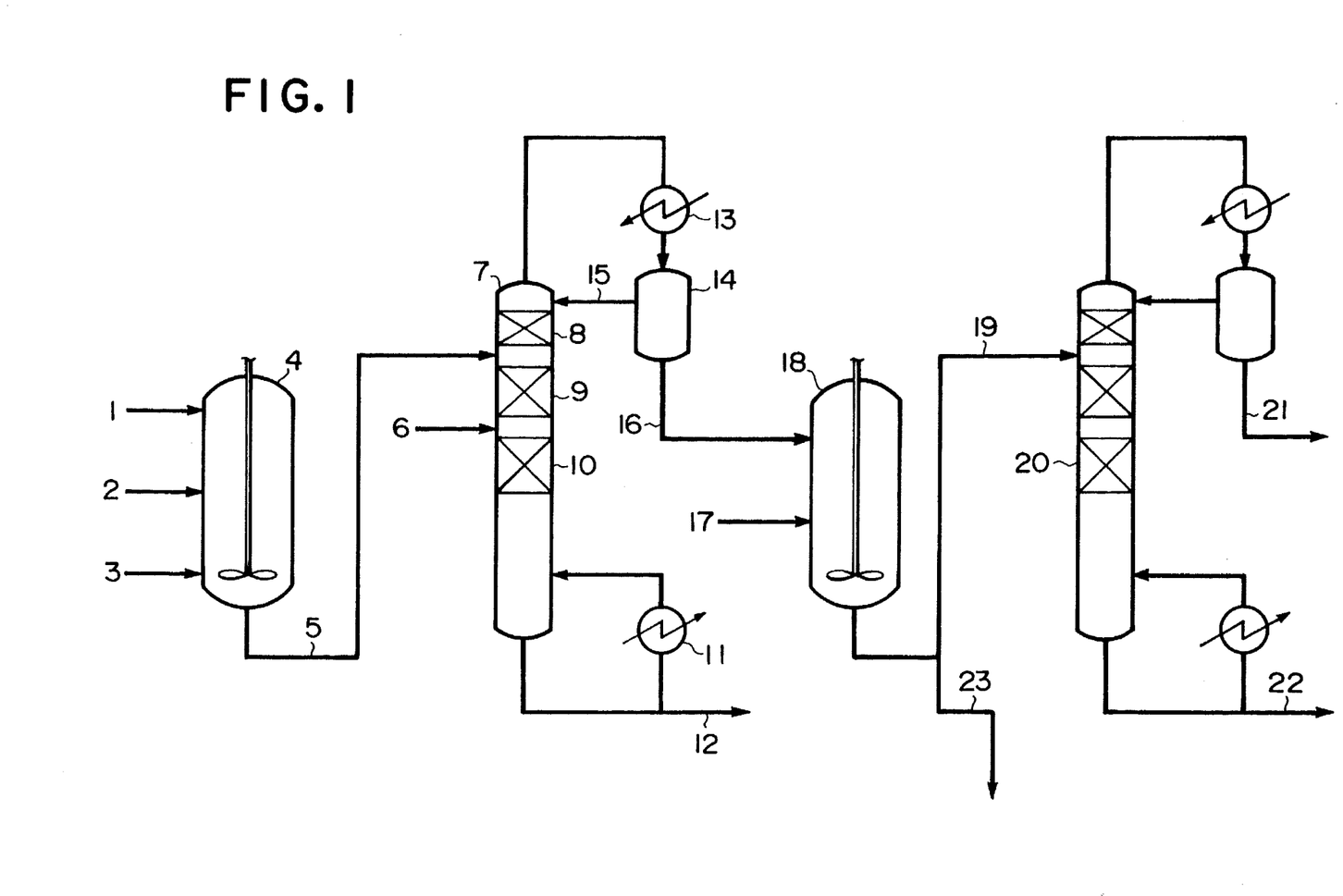
FIG. 1 is a flow chart following the flow of the process comprising the step of synthesizing an acyl fluoride, the step of distilling the acyl fluoride, the step of esterification and the step of recovering hydrogen fluoride, provided by the present invention.

FIG. 1 shows the flow chart of the process for the production of esters, provided by the present invention, the process comprising (i) an acyl fluoride synthesis step in which the olefin and carbon monoxide are allowed to react in the presence of hydrogen fluoride, (ii) an acyl fluoride distillation step in which the reaction solution containing the formed acyl fluoride is distilled together with the saturated hydrocarbon having a higher boiling point than the acyl fluoride and being inert to the acyl fluoride, and (iii) an esterification step in which a mixture of the hydrogen fluoride and acyl fluoride, separated in the distillation step is allowed to react with the alcohol.

In the acyl fluoride synthesis step shown in FIG. 1, hydrogen fluoride is fed from a flow path 1 to an acyl fluoride synthesis reactor 4, and carbon monoxide is charged into the reactor through a flow path 3 up to a predetermined pressure. Then, an olefin is fed through a flow path 2 to synthesize an acyl fluoride.

In the next acyl fluoride distillation step, the reaction solution containing the acyl fluoride is introduced into an acyl fluoride distillation column 7 through a flow path 5, and the saturated hydrocarbon is charged into the acyl fluoride distillation column 7 through a flow path 6.

The distillation column 7 includes a packed column and a plate column. When the packed column is used, it is divided into an upper packed portion 8, an intermediate packed portion 9 and a lower packed portion 10 for increasing the distillation efficiency. And, the reaction mixture containing the acyl fluoride is fed into a portion between the upper packed portion 8 and the intermediate packed portion 9, and the saturated hydrocarbon is fed into a portion between the intermediate packed portion 9 and the lower packed portion 10.

In the distillation column, the heating is effected with a reboiler 11, whereby steams of HF, acyl fluoride and saturated hydrocarbon are obtained from the top of the distillation column, totally condensed in a condenser 13 and introduced into a separator 14. In the separator 14, there is a complex of HF and acyl fluoride, and the steams are separated into two layers, a layer of the complex and a layer of the saturated hydrocarbon, due to a specific gravity difference between the complex and the saturated hydrocarbon. The saturated hydrocarbon in the upper layer portion is drawn through a flow path 15 and recycled to the distillation column. HF and the acyl fluoride are drawn through a flow path 16, and introduced into an esterification reactor 18.

In the esterification step, the HF and the acyl fluoride are fed into the esterification reactor 18 through the flow path 16, and the alcohol is fed into the esterification reactor 18 through a flow path 17, to carry out the esterification.

After the esterification, the esterification reaction solution is introduced into a catalyst recovery distillation column 20 through a flow path 19. HF is recovered from a column top 21, and esters are obtained from a column bottom 22. In another method, the esterification reaction solution is poured into ice water through a flow path 23, and esters can be separated from an oil layer.

Figure 2:
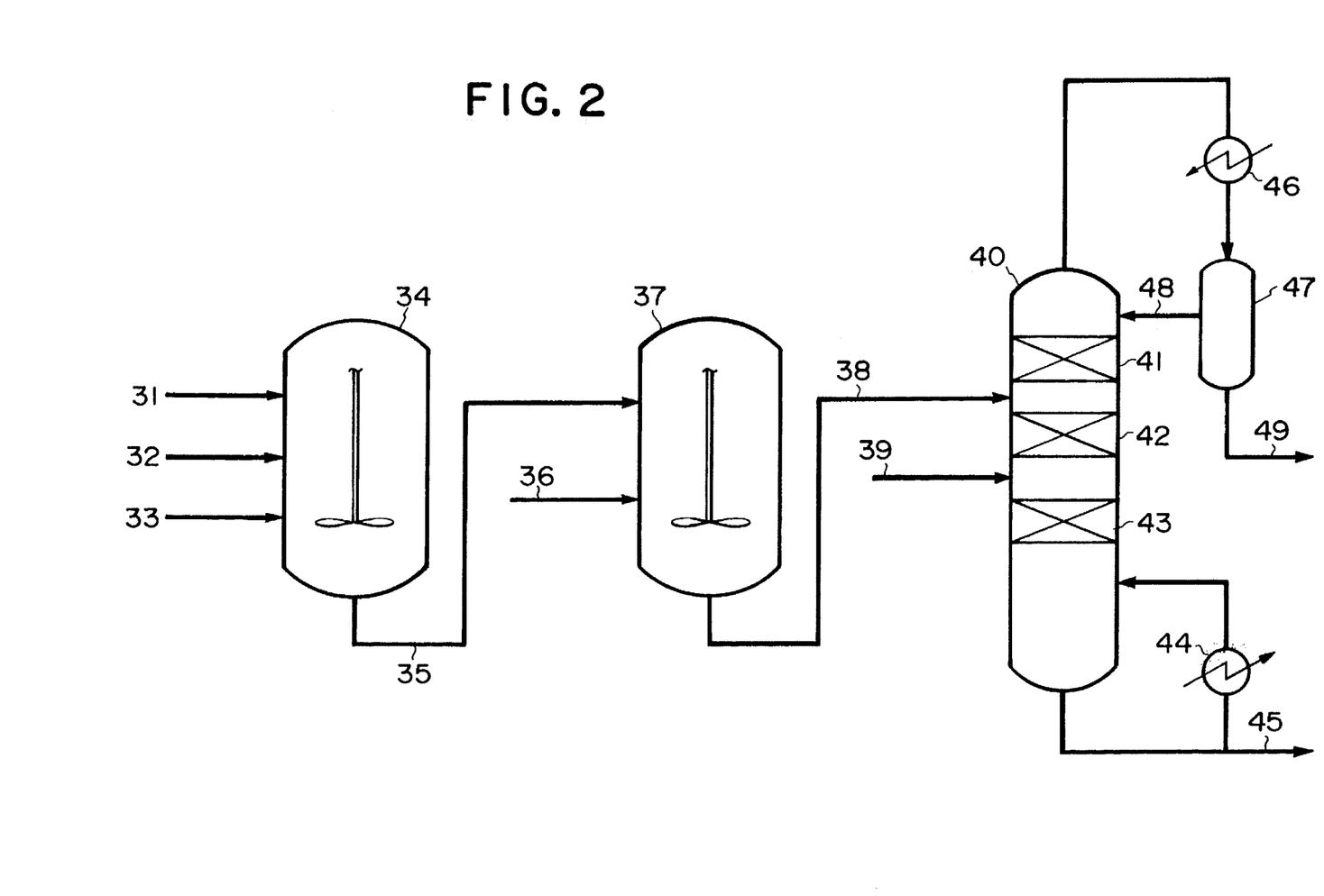
FIG. 2 is a flow chart showing the flow of the process comprising the step of synthesizing an acyl fluoride, the step of esterification and the step of hydrogen fluoride, provided by the present invention.

FIG. 2 shows the flow chart of the process of the present invention, which comprises allowing the olefin and carbon monoxide in the presence of hydrogen fluoride to form an acyl fluoride, allowing the acyl fluoride and the alcohol to react to form esters, and distilling the reaction solution containing the esters under the reflux of a saturated hydrocarbon having a higher boiling point than the acyl fluoride and being inner to the acyl fluoride to decompose the reaction solution into the esters and hydrogen fluoride.

In the acyl fluoride synthesis step shown in FIG. 2, hydrogen fluoride is fed into an acyl fluoride reactor 34 through a flow path 31 and carbon monoxide is charged into the acyl fluoride reactor 34 through a flow path 33 up to a predetermined pressure. Then, the olefin is fed through a flow path 32 to synthesize an acyl fluoride. The reaction solution containing the acyl fluoride is introduced into the esterification step.

In the esterification step, the reaction solution containing the acyl fluoride is fed into an esterification reactor 37 through a flow path 35, and the alcohol is fed into the esterification reactor 37 through a flow path 36, to carry out the esterification.

After the reaction, the esterification reaction solution is introduced into an HF-recovery distillation column 40 through a flow path 38, and the saturated hydrocarbon is introduced into the HF-recovery distillation column 40 through a flow path 39. The HF-recovery distillation column 40 includes a packed column and a plate column. When a packed column is used, it is divided into an upper packed portion 41, an intermediate packed portion 42 and a lower packed portion 43 for increasing the distillation efficiency. And, the esterification reaction solution is fed into a portion between the upper packed portion 41 and the intermediate packed portion 42, and the saturated hydrocarbon is fed into a portion between the intermediate packed portion 42 and the lower packed portion 43.

In the HF-recovery distillation column, the heating is effected with a reboiler 44, whereby steams of HF and saturated hydrocarbon are obtained from the top of the distillation column, totally condensed in a condenser 46 and introduced into a separator 47. In the separator 47, the hydrogen fluoride forms one layer, and the saturated hydrocarbon forms another layer, due to a specific gravity difference between the hydrogen fluoride and the saturated hydrocarbon. The saturated hydrocarbon in the upper layer portion is drawn through a flow path 48 and recycled to the distillation column. The hydrogen fluoride is drawn through a flow path 49 and recycled. Esters, byproducts and saturated hydrocarbon are drawn through a flow path 45 connected to the column bottom.

Figure 3:
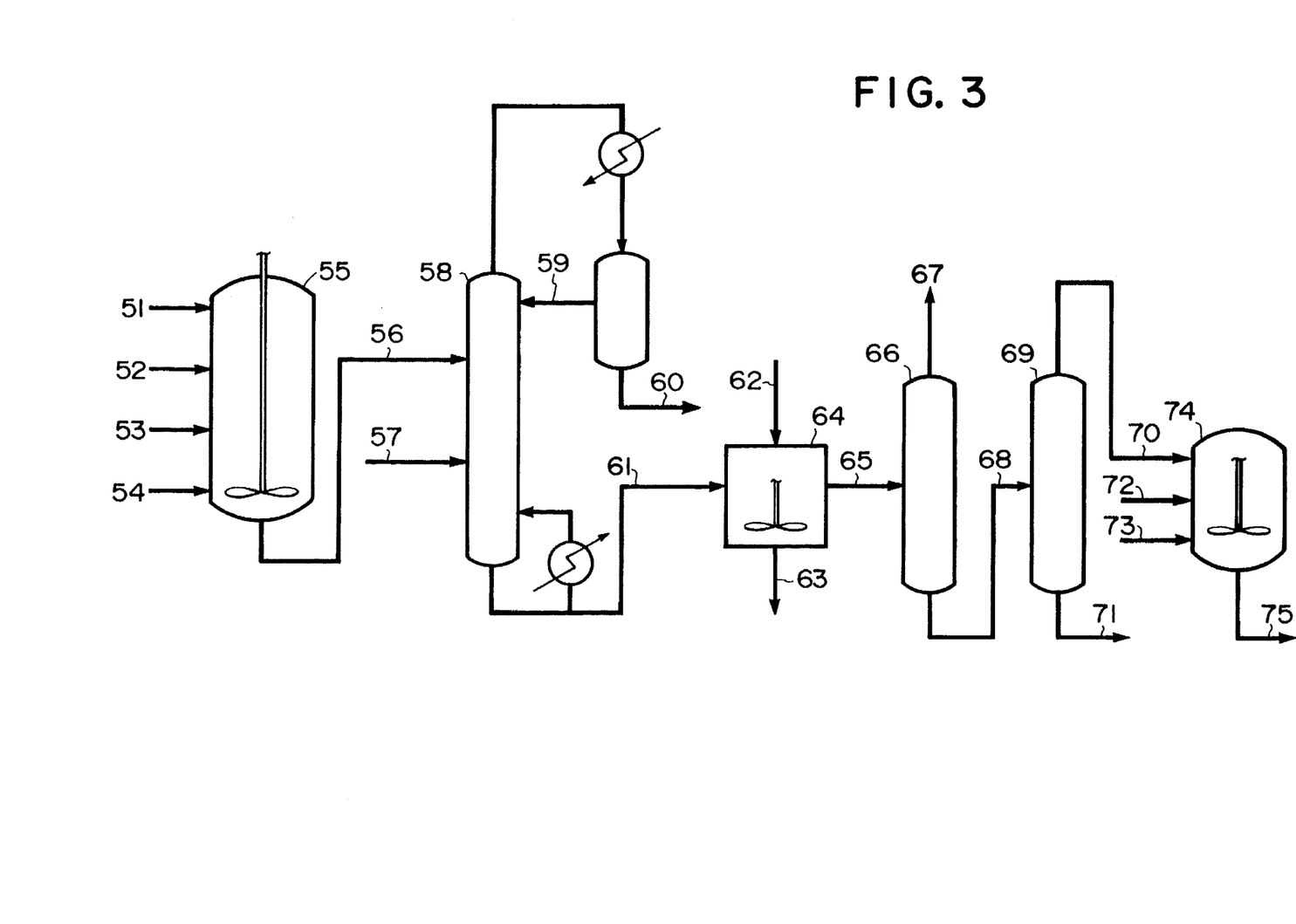
FIG. 3 is a flow chart showing the flow of the process comprising the step of synthesizing an acyl fluoride, the step of esterification, the step of recovering hydrogen fluoride, the step of washing a reaction solution containing esters with water and distilling the reaction solution and the step of catalytically hydrogenation-treating the esters.

FIG. 3 is the flow chart of the process for the production of esters, provided by the present invention, which comprises allowing the olefin, carbon monoxide and the alcohol to react in the presence of hydrogen fluoride, distilling the resultant reaction solution under the reflux of the saturated hydrocarbon to recover hydrogen fluoride, washing the reaction solution with water, distilling and purifying the reaction solution, and carrying out the catalytic hydrogenation treatment.

In FIG. 3, the method (1) is carried out as follows. Hydrogen fluoride is fed into a reactor 55 through a flow path 51 and carbon monoxide is charged into the reactor 55 through a flow path 53 up to a predetermined pressure. Then, the olefin is fed through a flow path 52 to synthesize an acyl fluoride. After the synthesis is completed, the pressure in the reactor is reduced to atmospheric pressure, and then, the alcohol is fed through a flow path 54 to synthesize an ester. Further, ester(s) may be synthesized by the method (2) or (3) as follows. In the reactor 55, the olefin, carbon monoxide and alcohol are allowed to react in the presence of hydrogen fluoride.

After the ester(s) is synthesized, the reaction solution and hydrogen fluoride are introduced into an HF-recovery distillation column 58 through a flow path 56, and the saturated hydrocarbon is introduced into the HF-recovery distillation column through a flow path 57. Hydrogen fluoride and saturated hydrocarbon are obtained from the top of the HF-recovery distillation column 58, and the saturated hydrocarbon is recycled to the HF-recovery distillation column 58 through a flow path 59. The hydrogen fluoride is drawn through a flow path 60, and recycled. The reaction solution and saturated hydrocarbon are drawn through a flow path 61 connected to the bottom of the distillation column, and introduced into a washing vessel 64.

Washing water is introduced into the washing vessel through a flow path 62 to wash the reaction solution, and the reaction solution is allowed to stand. Then, the washing water is drawn through a flow path 63. The washed reaction solution and saturated hydrocarbon are drawn through a flow path 65.

In a purification distillation column (I) 66, first, saturated hydrocarbon laving a low boiling point is distilled off through a flow path 67, and recycled. The esters and components having a high boiling point from the column bottom are introduced into a purification distillation column (II) 69 through a flow path 68. In the purification distillation column (II), the ester(s) is distilled out through the column top, and introduced into a hydrogenation treatment vessel 64 through a flow path 70. Components having a high boiling point are drawn through a flow path 71 connected to the bottom of the purification distillation column (II). In the hydrogenation treatment vessel 74, the ester fraction introduced through the flow path 70 is catalytically hydrogenation-treated in the presence of a catalyst introduced through a flow path 72 and hydrogen introduced through a flow path 73. The esters and catalysts are drawn through a flow path 75, and filtered to separate them.

In the process of the present invention, esters can be obtained from an olefin, carbon monoxide and an alcohol at high yields by the reaction thereof at a low temperature for a short period of time. Further, in the process of the present invention, the reaction rate is high so that the reactor therefor can be decreased in size, and hydrogen fluoride used as a catalyst can be easily separated from the reaction product and recycled. Therefore, esters can be highly advantageously produced from the industrial viewpoint.

Further, in the process of the present invention, the step of producing esters is divided into the acyl fluoride synthesis step in which the olefin and carbon monoxide are allowed to react in the presence of hydrogen fluoride and the esterification step in which the acyl fluoride synthesis solution is allowed to react with the alcohol, and in the acyl fluoride synthesis step, an olefin having at least 4 carbon atoms is used as the olefin and the reaction temperature or pressure is changed, whereby the kinetic viscosity of a mixture of esters can be adjusted, and there can be obtained a mixture of esters having a kinetic viscosity required as an engine oil or a refrigerating machine oil.

That is, in the process of the present invention, it is not necessary to change the combinations of fatty acids and alcohols or mix a low-viscosity ester and a high-viscosity ester for the adjustment of the kinetic viscosity, and mixtures of esters for use as various engine oils and refrigerating machine oil can be industrially advantageously produced.

In the present invention, the process for the production of esters is divided into the acyl fluoride synthesis step in which the olefin and carbon monoxide are allowed to react in the presence of hydrogen fluoride and the esterification step in which the acyl fluoride obtained is allowed to react with the alcohol, and the reaction solution from the acyl fluoride synthesis step is distilled under the reflux of a saturated hydrocarbon which has a higher boiling point than the acyl fluoride and is inert to the acyl fluoride. As a result, industrially advantageously, the following effects are obtained. a) Since the next step of esterification can be carried out at a low temperature for a short period of time, the amount of byproducts is small, and the yield of the esters improves. b) Since the amount of byproducts from the esterification is small, the purification can be easily carried out, and high-purity esters can be obtained. c) The amount of energy used for heating the reaction solution for recovering hydrogen fluoride as a catalyst can be reduced.

Further, in the process of the present invention, the olefin and carbon monoxide are allowed to react in the presence of hydrogen fluoride to form an acyl fluoride, the acyl fluoride is allowed to react with the alcohol to produce esters, and a complex of the ester(s) and hydrogen fluoride is decomposed by distilling the reaction solution under the reflux of a saturated hydrocarbon which has a higher boiling point than the acyl fluoride and is inert to the acyl fluoride, whereby the hydrogen fluoride can be efficiently recycled, and the esters can be advantageously produced.

Moreover, in the present invention, the reaction solution from which the hydrogen fluoride has been recovered is purified by washing it with water and distillation, and the purified reaction solution is catalytically hydrogenation-treated, whereby the ester(s) has an acid value of 0.02 mgKOH/g or less and is decolored. According to the process of the present invention, therefore, ester(s) for use as an engine oil or a refrigerating machine oil can be advantageously produced.

DESCRIPTION OF THE PREFERRED EMBODIMENTS

The present invention will be further detailed hereinafter with reference to Examples. However, the present invention shall not be limited to these Examples.

In Examples, the acid value was analyzed by a titration method using an N/25 potassium hydroxide solution, the hydroxyl value was analyzed by a pyridine-acetic anhydride method, the kinetic viscosity was measured with an Ubbelohde viscometer, and the color of an ester was measured with an ASTM color tester.

Example 1

Esters were produced with a two-liter autoclave of stainless steel, having a stirrer, three inlet nozzles provided in an upper portion, one outlet nozzle provided in a bottom portion and a jacket for adjusting the temperature inside.

First, the above autoclave was flushed with carbon monoxide, and then 420 g (21 mol) of hydrogen fluoride was introduced. The hydrogen fluoride was cooled to −10° C., and the pressure inside the autoclave was increased up to 20 kg/cm$^2$ with carbon monoxide. While this reaction temperature was maintained and while carbon monoxide was introduced so as to maintain the above pressure, 160 g (1.9 mol) of 1-hexene was fed through a gaseous phase in the autoclave over about 60 minutes, and after the feeding finished, the mixture was continuously stirred for about 20 minutes. The amount of carbon monoxide absorbed by the reaction was 39.2 g (1.4 mol), which was calculated on the basis of a weight difference in a carbon monoxide measuring vessel.

Then, the pressure inside the autoclave was reduced to atmospheric pressure to purge unreacted carbon monoxide, and 48 g (1.5 mol) of methanol was fed into the autoclave with a pump over about 30 minutes. The reaction temperature was set at 10° C., and the mixture was stirred for 2 hours. After the reaction, the reaction solution was poured into ice water to separate an oil layer. The obtained oil layer was washed with water and distilled at 20 mmHg to give 197 g of a fraction having a boiling point of 50° to 53° C. This fraction was analyzed by gas chromatography to show that the fraction was an isomer mixture containing 25% by weight of 2,2-dimethylpentanoic acid methyl ester, 8% by weight of 2-ethyl-2-methyl-butanoic acid methyl ester, 47% by weight of 2-ethylpentanoic acid methyl ester and 20% by weight of 2-methylhexanoic acid methyl ester. The yield of the esters based on the equivalent of the fed 1-hexene was 72 mol %.

Example 2

The esterification was carried out in the same manner as in Example 1 except that the methanol was replace with ethanol, and an ester fraction was separated in the same manner as in Example 1 to give 214 g of an isomer mixture containing four ethyl esters, i.e., 25% by weight of 2,2-dimethylpentanoic acid ethyl ester, 8% by weight of 2-ethyl-2-methyl-butanoic acid ethyl ester, 47% by weight of 2-ethylpentanoic acid ethyl ester and 20% by weight of 2-methylhexanoic acid ethyl ester. The yield of the esters based on the equivalent of the fed 1-hexene was 71 mol %.

Example 3

The esterification was carried out in the same manner as in Example 1 except that the methanol was replaced with n-propanol, and then, the resultant solution of esters in hydrogen fluoride was distilled through an HF-recovery distillation column (inner diameter 55 mm, height 1,000 mm, packed with Teflon packing ring) at a pressure of 2 kg/cm$^2$G at a column bottom temperature of 120° C. under the reflux of hexane to recover hydrogen fluoride.

A hexane solution containing esters and an excess of propanol was drawn from the column bottom, distilled and purified to give 231 g of an isomer mixture containing four n-propyl esters, i.e., 25% by weight of 2,2-dimethylpentanoic acid propyl ester, 8% by weight of 2-ethyl-2-methylbutanoic acid propyl ester, 47% by weight of 2-ethylpentanoic acid propyl ester and 20% by weight of 2-methylhexanoic acid propyl ester. The yield of the esters based on the equivalent of the fed 1-hexene was 71 mol %.

Example 4

The esterification was carried out in the same manner as in Example 3 except that the n-propanol was replaced with trimethylolpropane, and hydrogen fluoride was recovered from the resultant hydrogen fluoride solution of esters through the same HF-recovery distillation column as that used in Example 3. The column bottom solution was simple-distilled to give a 208 g fraction having a boiling point, at 2–3 mmHg, of 220° to 230° C., and this fraction was analyzed by gas chromatography to show an isomer mixture having a triester purity of at least 99%. The yield of the esters on the basis of the fed 1-hexene was 70 mol %. This isomer mixture had the following physical properties, a kinetic viscosity of 23.6 cst (40° C.), a specific gravity of 0.954 (20/20° C.) and a hydroxyl value of not more than 5 mgKOH/g.

Example 5

The same reaction between 1-hexene and carbon monoxide as that in Example 1 was carried out at 10° C. The esterification of the resultant reaction solution and methanol and the purification were carried out in the same manner as in Example 1 to give 184 g of a fraction. The resultant fraction was analyzed by gas chromatography to show that the fraction was an isomer mixture containing 40% by weight of 2,2-dimethylpentanoic acid methyl ester, 13% by weight of 2-ethyl-2-methyl-butanoic acid methyl ester, 32% by weight of 2-ethylpentanoic acid methyl ester and 15% by weight of 2-methylhexanoic acid methyl ester. The yield of the esters based on the equivalent of the fed 1-hexene was 67 mol %.

Example 6

The same reaction between 1-hexene and carbon monoxide as that in Example 1 was carried out at 35° C. The esterification of the resultant reaction solution and methanol and the purification were carried out in the same manner as in Example 1 to give 170 g of a fraction. The resultant fraction was analyzed by gas chromatography to show that the fraction was an isomer mixture containing 53% by weight of 2,2-dimethylpentanoic acid methyl ester, 20% by weight of 2-ethyl-2-methyl-butanoic acid methyl ester, 17% by weight of 2-ethylpentanoic acid methyl ester and 10% by weight of 2-methylhexanoic acid methyl ester. The yield of the esters based on the equivalent of the fed 1-hexene was 62 mol %.

Example 7

The same reaction between 1-hexene and carbon monoxide as that in Example 1 was carried out at a pressure of 50 kg/cm$^2$G at −13° C. The esterification of the resultant reaction solution and methanol and the purification were carried out in the same manner as in Example 1 to give 219 g of a fraction. The resultant fraction was analyzed by gas chromatography to show that the fraction was an isomer mixture containing 13% by weight of 2,2-dimethylpentanoic acid methyl ester, 4% by weight of 2-ethyl-2-methyl-butanoic acid methyl ester, 58% by weight of 2-ethylpentanoic acid methyl ester and 25% by weight of 2-methylhexanoic acid methyl ester. The yield of the esters based on the equivalent of the fed 1-hexene was 80 mol %.

Example 8

The same autoclave as that used in Example 1 was first flushed with carbon monoxide, and then 39 g (1.2 mol) of methanol and 480 g (24 mol) of hydrogen fluoride were introduced. The temperature inside the autoclave was increased up to 45° C. and while this temperature was maintained, the pressure inside the autoclave was increased up to 20 kg/cm$^2$G with carbon monoxide. While the above reaction temperature and pressure were maintained, 63 g (1.5 mol) of propylene was fed into a gaseous phase of the autoclave over about 60 minutes, and further, the mixture was allowed to react for 1 hour. After the reaction finished, the reaction solution was poured into ice water, and a separated oil layer was isolated, washed with a 5% sodium hydroxide aqueous solution and then washed with water. The washed oil layer was distilled to give 115 g of isobutyric acid methyl ester as a fraction having a boiling point of 92° to 94° C. The yield of the ester on the basis of the fed isopropylene equivalent was 75 mol %.

Example 9

The same autoclave as that used in Example 1 was first flushed with carbon monoxide, and then 480 g (24 mol) of hydrogen fluoride was introduced. The temperature inside the autoclave increased up to 45° C. and while this temperature was maintained, the pressure inside the autoclave was increased up to 20 kg/cm$^2$G with carbon monoxide. While the above reaction temperature and pressure were maintained, 39 g (1.2 mol) of methanol and 63 g (1.5 mol) of propylene were fed into a gaseous phase of the autoclave over about 60 minutes, and further, the mixture was allowed to react for 1 hour. After the reaction finished, the reaction solution was poured into ice water, and a separated oil layer was isolated, washed with a 5% sodium hydroxide aqueous solution and then washed with water. The washed oil layer was distilled to give 112 g of isobutyric acid methyl ester as a fraction having a boiling point of 92° to 94° C. The yield of the ester on the basis of the fed isopropylene equivalent was 73 mol %.

Example 10

Esters were produced with a one-liter autoclave of stainless steel, having a stirrer, three inlet nozzles provided in an upper portion, one outlet nozzle provided in a bottom portion and a jacket for adjusting the temperature inside.

First, the above autoclave was flushed with carbon monoxide, and then 210 g (10.5 mol) of hydrogen fluoride was introduced. The hydrogen fluoride was cooled to −18° C., and the pressure inside the autoclave was increased up to 20 kg/cm$^2$ with carbon monoxide. While this reaction temperature was maintained and while carbon monoxide was introduced so as to maintain the above pressure, 90.7 g (0.81 mol) of 1-octene was fed through a gaseous phase in the autoclave over about 30 minutes, and after the feeding finished, the mixture was continuously stirred for about 20 minutes until no absorption of carbon monoxide was observed. The amount of carbon monoxide absorbed by the reaction was 17.6 g (0.63 mol), which was calculated on the basis of a weight difference in a carbon monoxide measuring vessel.

Then, the pressure inside the autoclave was reduced to atmospheric pressure to purge unreacted carbon monoxide, and 21.5 g (0.158 mol) of pentaerythritol was fed into the autoclave at 0° C. over about 20 minutes, and the mixture was stirred for 2 hours. After the reaction finished, the reaction solution was poured into ice water to separate an oil layer. The obtained oil layer was washed with water and distilled. The main fraction was analyzed by gas chromatography to show that it was 104.4 g of a tetraester isomer mixture having a purity of at least 99%. The yield of the esters based on the fed 1-octene was 74.1 mol %. The above-obtained isomer mixture had the following physical properties, a kinetic viscosity of 62 cst (40° C.) and a hydroxyl value of not more than 2 mgKOH/g.

Example 11

103.5 Grams of a tetraester isomer mixture having a purity of at least 99% was obtained in the same manner as in Example 10 except that the temperature for the synthesis of acyl fluoride was changed to −7° C., to give 103.5 g of a tetraester isomer mixture having a purity of at least 99%. The yield of the esters based on the fed 1-octene was 73.5 mol %. The above-obtained isomer mixture had the following physical properties, a kinetic viscosity of 70 cst (40° C.) and a hydroxyl value of not more than 2 mgKOH/g.

Example 12

103.5 Grams of a tetraester isomer mixture having a purity of at least 99% was obtained in the same manner as in Example 10 except that the temperature for the synthesis of acyl fluoride was changed to −1° C. The yield of the esters based on the fed 1-octene was 73.2 mol %. The above-obtained isomer mixture had the following physical properties, a kinetic viscosity of 78 cst (40° C.) and a hydroxyl value of not more than 2 mgKOH/g.

Example 13

90.1 Grams of a triester isomer mixture having a purity of at least 99% was obtained in the same manner as in Example 10 except that the 1-octene was replaced with 1-hexene, that the pentaerythritol was replaced with trimethylolpropane and that the temperature for the acyl fluoride synthesis was changed to −13° C. The yield of the esters based on the fed 1-hexene was 71.0 mol %. The above-obtained isomer mixture had the following physical properties, a kinetic viscosity of 22 cst (40° C.) and a hydroxyl value of not more than 2 mgKOH/g.

Example 14

A triester isomer mixture having a purity of at least 99% was obtained in the same manner as in Example 13 except that the pressure for the acyl fluoride synthesis was changed to 50 kg/cm$^2$G. The yield of the esters based on the fed 1-hexene was 75.2 mol %. The above-obtained isomer mixture had the following physical properties, a kinetic viscosity of 13 cst (40° C.) and a hydroxyl value of not more than 2 mgKOH/g.

Example 15

Esters were produced with two one-liter autoclaves of stainless steel, having a stirrer, three inlet nozzles provided in an upper portion, one outlet nozzle provided in a bottom portion and a jacket for adjusting the temperature inside and one distillation column of stainless steel, which had a column diameter of 30 mm and a height of 1,000 mm and was packed with ½ inch Teflon packing ring.

First, the autoclave for acyl fluoride synthesis was flushed with carbon monoxide, and then 210 g (10.5 mol) of hydrogen fluoride was introduced. The hydrogen fluoride was cooled to −15° C., and the pressure inside the autoclave was increased up to 20 kg/cm$^2$ with carbon monoxide. While this reaction temperature was maintained and while carbon monoxide was introduced so as to maintain the above pressure, 91 g (0.81 mol) of 1-octene was fed through a gaseous phase in the autoclave over about 30 minutes, and after the feeding finished, the mixture was continuously stirred for about 20 minutes until no absorption of carbon monoxide was observed. The amount of carbon monoxide absorbed by the reaction was 17.6 g (0.63 mol), which was calculated on the basis of a weight difference in a carbon monoxide measuring vessel.

Then, the above-obtained reaction solution containing an acyl fluoride and n-decane were fed to the other distillation column, and the reaction solution was distilled under the reflux of the n-decane. The hydrogen fluoride and acyl fluoride were recovered from the column top and introduced to the esterification reactor. Byproducts and n-decane were drawn from the column bottom.

22 Grams (0.69 mol) of methanol was fed into the esterification reactor with a pump at 0° C. over about 15 minutes, and the mixture was allowed to react for 2 hours. After the reaction finished, the reaction solution was withdrawn and poured into ice water to separate an oil layer. The obtained oil layer was washed with an alkali, but was not distilled or purified. The so-obtained oil layer was analyzed by gas chromatography to show that the oil layer was 108 g of an isomer mixture of six methyl esters such as 9% by weight of 2-methyl-2-propylpentanoic acid methyl ester, 14% by weight of 2,2-dimethylheptanoic acid methyl ester, 19% by weight of 2-methyl-2-ethylhexanoic acid methyl ester, 24% by weight of 2-propylhexanoic acid methyl ester, 26% by weight of 2-ethylheptanoic acid methyl ester and 8% by weight of 2-methyloctanoic acid methyl ester. The yield of the esters on the basis of the fed 1-octene was 77.4 mol %.

Example 16

The same reaction solution containing an acyl fluoride as that obtained in Example 15 was not distilled. 22 Grams (0.69 mol) of methanol was introduced into the reaction solution with a pump at an atmospheric pressure at 0° C. over about 15 minutes, and the mixture was allowed to react in the same manner as in Example 15. After the reaction, the esterification reaction solution was withdrawn and poured in to ice water, and an oil layer was separated and washed with an alkali. The oil layer was analyzed by gas chromatography to show a peak of byproducts in addition to a peak of methyl ester. The oil layer was hence distilled to separate a methyl ester fraction. The methyl ester fraction was analyzed by gas chromatography to show that it was 102 g of an isomer mixture containing the same six methyl esters as those in Example 15. The yield of the esters on the basis of the fed 1-octene was 73.0 mol %.

Example 17

Esters were obtained in the same manner as in Example 15 except that the methanol was replaced with ethanol. As a result, there was obtained 117 g of an isomer mixture of six methyl esters such as 9% by weight of 2-methyl-2-propylpentanoic acid ethyl ester, 14% by weight of 2,2-dimethylheptanoic acid ethyl ester, 19% by weight of 2-methyl-2- ethylhexanoic acid ethyl ester, 24% by weight of 2-propylhexanoic acid ethyl ester, 26% by weight of 2-ethylheptanoic acid ethyl ester and 8% by weight of 2-methyloctanoic acid ethyl ester. The yield of the esters on the basis of the fed 1-octane was 77.4 mol %.

Example 18

The synthesis of an acyl fluoride was carried out at −15° C. in the same manner as in Example 15 except that the 1-octene was replaced with 1-butene. The resultant reaction solution and heptane were fed into a distillation column, and the reaction solution was distilled under the reflux of the heptane to recover hydrogen fluoride and acyl fluoride from the column top. The recovered solution was subjected to an esterification with methanol for 2 hours, and the reaction mixture was poured into ice water, and the resultant oil layer was washed with an alkali. The oil layer was analyzed by gas chromatography to show that it contained at least 99% by weight of 2-methylbutanoic acid methyl ester, and the yield thereof was 69.4 g. The yield of the ester on the basis of the fed 1-butene was 73.8 mol %.

Example 19

The ester synthesis was carried out in the same manner as in Example 18 except that the temperature for the synthesis of an acyl fluoride was changed to 15° C. The resultant oil layer was analyzed by gas chromatography to show that it was an isomer mixture containing 95% by weight of 2-methylbutanoic acid methyl ester and 5% by weight of 2,2-dimethylpropanonic acid methyl ester, and the yield thereof was 65.0 g. The yield of the esters on the basis of the fed 1-butone was 69.1 mol %.

Example 20

Esters were synthesized in the same manner as in Example 15 except that the reaction between 1-octene and carbon monoxide was carried out at a pressure of 50 kg/cm$^2$G. The resultant oil layer was analyzed by gas chromatography to show that it was 115 g of an isomer mixture containing 6% by weight of 2-methyl-2-propylpentanoic acid methyl ester, 11% by weight of 2,2-dimethylheptanoic acid methyl ester, 17% by weight of 2-methyl-2-ethylhexanoic acid methyl ester, 25% by weight of 2-propylhexanoic acid methyl ester, 28% by weight of 2-ethylheptanoic acid methyl ester and 13% by weight of 2-methyloctanoic acid methyl ester. The yield of the esters on the basis of the fed 1-octene was 82.5 mol %.

Example 21

Esters were produced with two one-liter autoclaves of stainless steel, having a stirrer, three inlet nozzles provided in an upper portion, one outlet nozzle provided in a bottom portion and a jacket for adjusting the temperature inside, as a reactor for the synthesis of an acyl fluoride and a reactor for the esterification and one distillation column of stainless steel, which had a column diameter of 30 mm and a height of 1,000 mm and was packed with ½ inch Teflon packing ring, as an HF-recovery distillation column.

First, the reactor for acyl fluoride synthesis was flushed with carbon monoxide, and then 210 g (10.5 mol) of hydrogen fluoride was introduced. The hydrogen fluoride was cooled to −15° C., and the pressure inside the autoclave was increased up to 20 kg/cm$^2$ with carbon monoxide. While this reaction temperature was maintained and while carbon monoxide was introduced so as to maintain the above pressure, 91 g (0.81 mol) of 1-octene was fed through a gaseous phase in the autoclave over about 30 minutes, and after the feeding finished, the mixture was continuously stirred for about 20 minutes until no absorption of carbon monoxide was observed. The amount of carbon monoxide absorbed by the reaction was 17.6 g (0.63 mol), which was calculated on the basis of a weight difference in a carbon monoxide measuring vessel.

Then, the above-obtained reaction solution containing an acyl fluoride and 32.8 g (0.315 mol) of neopentyl glycol were fed to the reactor for the esterification at atmospheric pressure at 0° C. over about 20 minutes, and the mixture was allowed to react for 2 hours. After the reaction finished, the resultant esterification reaction solution and n-decane were introduced to the HF-recovery distillation column, and the reaction solution was distilled under the reflux of the n-decane at a pressure of 0.5 kg/cm$^2$G at a column bottom temperature of 200° C. And, the hydrogen fluoride was recovered from the column top. The so-recovered hydrogen fluoride was analyzed to show that it had a purity of 99.5% by weight and contained 0.5% by weight of dissolved n-decane. The amount of the recovered hydrogen fluoride was 208.9 g, and the recovery ratio thereof was 99.5%.

Esters and n-decane were drawn from the column bottom and washed with water. The n-decane was removed by simple distillation, and the remainder was further rectified. The main fraction was analyzed by gas chromatography to show that it was 115.2 g of an isomer mixture having an ester purity of at least 99%. The yield of the esters on the basis of the fed 1-octene was 74.0 mol %. The above-obtained isomer mixture had the following physical properties, a kinetic viscosity of 10 cst (40° C.) and a hydroxyl value of not more than 2 mgKOH/g.

Example 22

An acyl fluoride was synthesized in the same manner as in Example 21 except that the 1-octene was replaced with 68.0 g (0.81 mol) of 1-hexene. Then, 31.1 g (0.30 mol) of neopentyl glycol was fed to carry out the esterification. After the esterification finished, the esterification reaction solution and n-nonane were introduced into an HF-recovery distillation column, and the esterification reaction solution was distilled under the reflux of the n-nonane at a pressure of 0.5 kg/cm$^2$G at a column bottom temperature of 175° C. And, hydrogen fluoride was recovered from the column top. The recovered hydrogen fluoride was analyzed to show it had a purity of 99.3% by weight, and contained 0.7% by weight of n-nonane. The amount of the recovered hydrogen fluoride was 208.7 g, and the recovery ratio thereof was 99.4%.

A solution of esters and n-nonane was drawn from the column bottom, and washed with water. The n-nonane was removed by simple distillation, and the remainder was rectified. The main fraction was analyzed by gas chromatography to show that it was an isomer mixture having an ester purity of at least 99%. The yield of the esters was 92.8 g. The yield of the esters on the basis of the fed 1-hexene was 70.0 mol %. The above-obtained isomer mixture had the following physical properties, a kinetic viscosity of 6 cst (40° C.) and a hydroxyl value of not more than 2 mgKOH/g.

Example 23

An acyl fluoride was synthesized at −10° C. in the same manner as in Example 21 except that the 1-octene was replaced with 45.4 g (0.81 mol) of 1-butene. 26.8 Grams (0.20 mol) of trimethylolpropane was introduced into the esterification reactor with a pump at atmospheric pressure at 0° C. over about 15 minutes, and the mixture was allowed to react for 2 hours.

The esterification reaction solution was distilled through the same HF-recovery distillation column as that used in Example 1 under the reflux of n-heptane at a pressure of 1.0 kg/cm$^2$G at a column bottom temperature of 130° C., and hydrogen fluoride was recovered from the column top. The recovered hydrogen fluoride was analyzed to show it had a purity of 99.3% by weight, and contained 0.7% by weight of n-heptane. The amount of the recovered hydrogen fluoride was 208.3 g, and the recovery ratio thereof was 99.2%.

A solution of esters and n-heptane was drawn from the column bottom, and washed with water. The n-heptane was removed by simple distillation, and the remainder was rectified to distill out a triester. The triester was analyzed by gas chromatography to show that it was an isomer mixture having a triester purity of at least 99%. The yield of the isomer mixture was 73.3 g. The yield of the esters on the basis of the fed 1-butene was 70.4 mol %. The above-obtained isomer mixture had the following physical properties, a kinetic viscosity of 13 cst (40° C.) and a hydroxyl value of not more than 2 mgKOH/g.

Example 24

The esterification was carried out in the same manner as in Example 21 except that the neopentyl glycol was replaced with ethanol. The esterification reaction solution was distilled through an HF-recovery distillation column under the reflux of n-decane. Hydrogen fluoride was recovered from the column top, and esters and n-decane were recovered from the column bottom and washed. The n-decane was removed by distillation, and the remainder was rectified to give 110 g of an oil, The recovered hydrogen fluoride was analyzed to show it had a purity of 99.3% by weight, and contained 0.7% by weight of n-decane. The amount of the recovered hydrogen fluoride was 208.3 g, and the recovery ratio thereof was 99.2%.

The above-obtained oil was analyzed by gas chromatography to show that it was an isomer mixture containing six esters such as 9% by weight of 2-methyl-2-propylpentanoic acid ethyl ester, 14% by weight of 2,2-dimethylheptanoic acid ethyl ester, 19% by weight of 2-methyl-2-ethylhexanoic acid ethyl ester, 24% by weight of 2-propylhexanoic acid ethyl ester, 26% by weight of 2-ethylheptanoic acid ethyl ester and 8% by weight of 2-methyloctanoic acid methyl ester. The yield of the esters on the basis of the fed 1-octene was 73.0 mol %.

Example 25

Esters were produced with two one-liter autoclaves of stainless steel, having a stirrer, three inlet nozzles provided in an upper portion, one outlet nozzle provided in a bottom portion and a jacket for adjusting the temperature inside, one distillation column (HF-recovery distillation column) of stainless steel, which had a column diameter of 30 mm and a height of 1,000 mm and was packed with ½ inch Teflon packing rin, and one 0.5-liter distillation column (for ester distillation) of glass.

First, one autoclave was flushed with carbon monoxide, and then 210 g (10.5 mol) of hydrogen fluoride was introduced. The hydrogen fluoride was cooled to −18° C., and the pressure inside the autoclave was increased up to 20 kg/cm$^2$ with carbon monoxide. While this reaction temperature was maintained and while carbon monoxide was introduced so as to maintain the above pressure, 91 g (0.81 mol) of 1-octene was fed through a gaseous phase in the autoclave over about 30 minutes, and after the feeding finished, the mixture was continuously stirred for about 20 minutes until no absorption of carbon monoxide was observed. The amount of carbon monoxide absorbed by the reaction was 17.6 g (0.63 mol), which was calculated on the basis of a weight difference in a carbon monoxide measuring vessel.

Then, the pressure inside the autoclave was reduced to atmospheric pressure, and 21.5 g (0.158 mol) of pentaerythritol was fed into the autoclave over about 30 minutes. The reaction temperature was set at 0° C., and the mixture was stirred for 2 hours. After the reaction finished, the resultant reaction solution and n-decane were introduced to the HF-recovery distillation column, and the reaction solution was distilled under the reflux of the n-decane at a pressure of 0.5 kg/cm$^2$G at a column bottom temperature of 200° C. And, hydrogen fluoride was recovered from the column top, and a solution of esters and n-decane was drawn from the column bottom and washed. The n-decane was removed by simple distillation, and the remainder was rectified to give 103.5 g of a yellow ester fraction. The ester fraction was measured for an acid value to show 0.055 mgKOH/g.

The above-obtained ester and 17.3 g of a 5% Ru/C catalyst (supplied by N. E. CHEMCAT Corporation) were charged into the autoclave, and the mixture was stirred at a temperature of 80° C. at a hydrogen pressure of 8 kg/cm$^2$G for 2 hours. The reaction solution was cooled to room temperature, and the catalyst was separated by filtration to give 100.5 g of a colorless transparent liquid. This liquid was analyzed by gas chromatography to show that it was an isomer mixture having a tetraester purity of at least 99%. The yield thereof on the basis of the fed 1-octene was 71.3 mol %. The obtained tetraester had an acid value of 0.012 mgKOH/g, a kinetic viscosity of 62 cst (40° C.), a hydroxyl value of not more than 2 mgKOH/g and a color, measured with an ASTM color tester, of L0.5.

Example 26

An ester was produced in the same manner as in Example 25 except that pentaerythritol was replaced with 32.9 g (0.316 mol) of neopentyl glycol.

The esterification reaction solution was rectified to give 114.6 g of a yellow ester fraction. This fraction had an acid value of 0.058 mgKOH/g.

The above-obtained ester fraction and 19.1 g of an Ni/diatomaceous earth catalyst [N103, Ni about 50%, supplied by Nikki Chemical Co., Ltd.) were charged into the autoclave, and the mixture was stirred at a temperature of 100° C. at a hydrogen pressure of 8 kg/cm$^2$G for 2 hours. The reaction solution was cooled to room temperature, and the catalyst was separated by filtration to give 113.4 g of a colorless transparent liquid. This liquid was analyzed by gas chromatography to show that it was an isomer mixture having a diester purity of at least 99%. The yield thereof on the basis of the fed 1-octene was 72.8 mol %. The obtained diester had an acid value of 0.013 mgKOH/g, a kinetic viscosity of 10 cst (40° C.), a hydroxyl value of not more than 2 mgKOH/g and a color, measured with an ASTM color tester, of L0.5.

Example 27

An ester was produced in the same manner as in Example 25 except that the 1-octene was replaced with 45.4 g (0.81 mol) of 1-butene, that the temperature for the synthesis of an acyl fluoride was set at −13° C. and that the pentaerythritol was replaced with 26.8 g (0.20 mol) of trimethylolpropane. The esterification reaction solution was rectified to give 73.3 g of a yellow ester fraction. This fraction had an acid value of 0.045 mgKOH/g.

The above-obtained ester fraction and 12.2 g of a 5% Pd/Cu catalyst (supplied by N. E. CHEMCAT Corporation) were charged into the autoclave, and the mixture was stirred at a temperature of 90° C. at a hydrogen pressure of 8 kg/cm$^2$G for 2 hours. The reaction solution was cooled to room temperature, and the catalyst was separated by filtration to give 71.3 g of a colorless transparent liquid. This liquid was analyzed by gas chromatography to show that it was an isomer mixture having a triester purity of at least 99%. The yield thereof on the basis of the fed 1-butene was 68.5 mol %. The obtained triester had an acid value of 0.010 mgKOH/g, a kinetic viscosity of 13 cst (40° C.), a hydroxyl value of not more than 2 mgKOH/g and a color, measured with an ASTM color tester, of L0.5.

Example 28

An ester was produced in the same manner as in Example 25 except that the 1-octene was replaced with 68.0 g (0.81 mol) of 1-hexene, that the temperature for the synthesis of an acyl fluoride was set at −13° C. and that the pentaerythritol was replaced with 26.8 g (0.20 mol) of trimethylolpropane. The esterification reaction solution was rectified to give 90.1 g of a yellow ester fraction. This fraction had an acid value of 0.047 mgKOH/g.

The above-obtained ester fraction and 15.0 g of a 2% Ru/Al catalyst (supplied by N. E. CHEMCAT Corporation) were charged into the autoclave, and the mixture was stirred at a temperature of 80° C. at a hydrogen pressure of 8 kg/cm$^2$G for 2 hours. The reaction solution was cooled to room temperature, and the catalyst was separated by filtration to give 89.2 g of a colorless transparent liquid. This liquid was analyzed by gas chromatography to show that it was an isomer mixture having a triester purity of at least 99%. The yield thereof on the basis of the fed 1-hexene was 70.4 mol %. The obtained triester had an acid value of 0.013 mgKOH/g, a kinetic viscosity of 22 cst (40° C.), a hydroxyl value of not more than 2 mgKOH/g and a color, measured with an ASTM color tester, of L0.5.

What is claimed is:

1. A process for the production of esters, which comprises the following steps:
   a first step in which an olefin and carbon monoxide are reacted in the presence of hydrogen fluoride to synthesize an acyl fluoride and
   a second step which allows the resultant acyl fluoride solution to react with an alcohol to form esters.

2. A process according to claim 1, wherein the hydrogen fluoride is used in an amount of 5 mol per mole of the olefin and is recycled from a reaction solution after the hydrogen fluoride is separated from the reaction solution and purified.

3. A process according to claim 1, wherein an olefin having at least 4 carbon atoms is used as the olefin in the step of synthesizing the acyl fluoride, and a reaction temperature or a reaction pressure at the step of synthesizing the acyl fluoride are changed to form esters having an adjusted kinetic viscosity.

4. A process for the production of esters wherein the process comprises a step of allowing an olefin and carbon monoxide to react in the presence of hydrogen fluoride to synthesize an acyl fluoride, a step of distilling a resultant reaction solution containing the acyl fluoride, together with a saturated hydrocarbon having a higher boiling point than the acyl fluoride and being inert to the acyl fluoride, and an esterification step of allowing a mixture of hydrogen fluoride and the acyl fluoride, separated in the distillation step, to react with an alcohol.

5. A process according to claim 4, wherein the saturated hydrocarbon is at least one member selected from the group consisting of hexane, heptane, octane, nonane and decane.

6. A process according to claim 4, wherein the step of distilling the resultant reaction solution containing the acyl fluoride is carried out together with the saturated hydrocarbon in an amount of 0.5 to 2.0 mol per mole of the olefin used in the step of allowing the olefin and carbon monoxide to react in the presence of hydrogen fluoride.

7. A process for the production of esters wherein the process comprises a step of allowing an olefin and carbon monoxide to react in the presence of hydrogen fluoride to synthesize an acyl fluoride, an esterification step of allowing the obtained acyl fluoride to react with an alcohol to form esters and a step of distilling the obtained reaction solution containing esters under reflux of a saturated hydrocarbon having a higher boiling point than the acyl fluoride and being inert to the acyl fluoride and separating and recovering the hydrogen fluoride to recycle the hydrogen fluoride.

8. A process according to claim 7, wherein the process further comprises a purification step of washing the reaction solution containing esters from which the hydrogen fluoride has been separated, with water and distilling the reaction solution, and a step of catalytic hydrogenation treatment of purified esters.

9. A process according to claim 8, wherein the esters have an acid value of 0.02 mgKOH/g or less and is decolored.

10. A process according to claim 1, wherein the alcohol is a monohydric or a polyhydric alcohol.

11. A process according to claim 1, wherein an equivalent ratio of OH group of the alcohol to the olefin is 2 or less.

* * * * *